United States Patent [19]
Okamoto

[11] Patent Number: 5,294,380
[45] Date of Patent: Mar. 15, 1994

[54] METHOD FOR PRODUCTION OF PLATE DENTURE

[76] Inventor: Kenji Okamoto, 333-5, Takashiro, Shiga-cho, Shiga-gun, Shiga-ken, Japan

[21] Appl. No.: 955,972

[22] Filed: Oct. 2, 1992

[51] Int. Cl.⁵ .................... A61C 13/10; B29C 45/00
[52] U.S. Cl. ..................... 264/18; 264/222; 264/327; 264/328.12; 264/328.16; 264/DIG. 30; 264/DIG. 65
[58] Field of Search .................... 264/16–19, 264/222, DIG. 30, 327, 328.12, 328.16, DIG. 65

[56] References Cited

U.S. PATENT DOCUMENTS

| | | | |
|---|---|---|---|
| 2,314,378 | 3/1943 | Van Rossem | 264/16 X |
| 2,696,023 | 12/1954 | Stott | 264/DIG. 65 X |
| 2,713,697 | 7/1955 | Willcox | 264/DIG. 65 |
| 2,806,253 | 9/1957 | Vernon et al. | 264/17 |
| 2,886,890 | 5/1959 | Schnell | 264/343 |
| 2,899,712 | 8/1959 | Smith | 264/18 |
| 3,001,240 | 9/1961 | Emerick | 264/18 |
| 3,036,340 | 5/1962 | Waddell, Jr. | 264/DIG. 65 X |
| 3,404,056 | 10/1968 | Baldwin | 264/322 X |
| 4,201,742 | 5/1980 | Hendry | 264/DIG. 65 X |
| 4,359,435 | 11/1982 | Kogure | 264/328.16 X |

OTHER PUBLICATIONS

Sales brochure for "GC Autocure", Japan by Kabushiki Kaisha GC (Sep. 21, 1967).
"The Dry Heat Curing Method", Thermally Polymerized Resin For Dental Plate And Production of Plate Denture, Japan, by Quintessence Publishing Co. (Sep. 10, 1991).

*Primary Examiner*—Karen Aftergut
*Attorney, Agent, or Firm*—Armstrong, Westerman, Hattori, McLeland & Naughton

[57] ABSTRACT

A method for producing a plate denture which includes heating a flask after embedding a wax denture and wax elimination to a temperature for polymerizing a heat-curable resin, the flask being an assembly including a first half shell having a plaster cast with a corresponding mucosal surface and a second half shell having a plaster cast with artificial teeth embedded therein. The method further including placing the heat-curable resin into the heated flask for polymerization while the flask is at an elevated temperature from the heating, and polymerizing the heat-curable resin in the heated flask. Wherein, during the step of heating the first half shell is heated to a higher temperature level in a range of temperature for polymerizing the heat-curable resin while the second half shell is heated to a lower temperature level in the range than the first half shell.

3 Claims, 3 Drawing Sheets

METHOD FOR PRODUCTION OF PLATE DENTURE

BACKGROUND OF THE INVENTION

1. Field of the Invention

The present invention relates to a method for production of a plate denture.

It is important that the surface area of a plate denture to be contacted with an oral mucosa (mucosal surface) have a dimensionally precise configuration. A dough-like resin undergoes shrinkage during polymerization so that an initially polymerized portion of the resin is cured into a layer with precise dimensions. For this reason, the polymerization of a dough like resin is preferably initiated from the side of a surface area of plaster cast corresponding to the mucosal surface of a plate denture.

2. Description of the Prior Art

Conventional methods for producing plate dentures include a method in which a dough-like resin is packed into the mold space of a flask after embedding a wax denture (flasking) and wax elimination, followed by immersion of the flask in hot water (heat-curing technique by water bath) and a method in which a flask with the dough packed therein is heated as disposed in between two heated plates (dry heating-curing technique).

According to these conventional methods, a dough-like resin is heated after supply into the mold space of the flask and therefore the polymerization is initiated in the resin locally at different times. When a dough-like resin placed in the mold space is heated, the temperature within the flask is elevated by heat transfer. A denture has a complicated shape which varies from person to person so that after supply, the dough reaches a polymerization-initiating temperature locally at different times. The initially polymerized portion of the dough is given a dimensionally precise configuration, while the other local portions are afforded a dimensionally less precise configuration. Consequently, these conventional methods produce plate dentures in which the configuration of a mucosal surface is not invariably dimensionally precise.

Conventionally it has been also practiced to place a dough-like resin into the mold space after flasking and wax elimination and to heat the flask from the side of a half shell of the flask having a surface area of plaster cast corresponding to the mucosal surface of a denture (hereinafter referred to as "corresponding mucosal surface of plaster cast") so that the polymerization is initiated from this side. However, this method allows the resin to initiate the polymerization locally at different times and to reach the polymerization-initiating temperature locally at different times and fails to invariably produce plate dentures having a mucosal surface of dimensionally precise configuration, by the same reasons as stated above concerning the above-mentioned conventional methods.

SUMMARY OF THE INVENTION

An object of the present invention is to provide a method for producing a plate denture in which the mucosal surface has a dimensionally precise configuration.

To achieve this and other objects of the present invention, the invention provides a method for producing a plate denture which comprises the steps of:

heating a flask after embedding a wax denture and wax elimination to a temperature for polymerizing a heat-curable dough-like resin, the flask being an assembly constructed by superposing into an enclosure a first half shell having a plaster cast with the corresponding mucosal surface and a second half shell having a plaster cast with artificial teeth embedded therein; and placing the resin into the heated flask for polymerization.

The flask of the invention can be heated to a predetermined temperature, for example, by introducing the flask into a constant temperature oven.

When a dough-like resin is charged into the flask already heated to a predetermined temperature in the invention, the dough is evenly and uniformly heated from the side of the corresponding mucosal surface of the plaster cast, whereby a plate denture is given a mucosal surface with a dimensionally more satisfactory and more precise configuration than when produced by the above-mentioned conventional techniques.

When the first half shell is heated to a higher temperature level in the range of a temperature for polymerizing a dough-like resin and the second half shell is heated to a lower temperature level in said range than the first half shell, the polymerization more preferably proceeds from the side of the corresponding mucosal surface of plaster cast, whereby the obtained denture would be provided with a mucosal surface of improved dimensionally precise configuration. In this method, the polymerization of the resin is preferably performed by placing the flask in a state of the first half shell placed at a lower position and the second half shell placed at an upper position. The method enables a more preferred progress of polymerization from the resin portion forming a mucosal surface of plate denture.

According to the method of the invention, the dough-like resin packed in the flask is almost instantly cured in a sprue on exposure to the temperature of previously heated flask, whereby the sprue is closed with the cured resin. Therefore the method of the invention gives a plate denture of dimensionally precise configuration without use of a device for preventing the back flow of resin at the sprue.

DETAILED DESCRIPTION OF THE PREFERRED EMBODIMENTS

Figure 1:
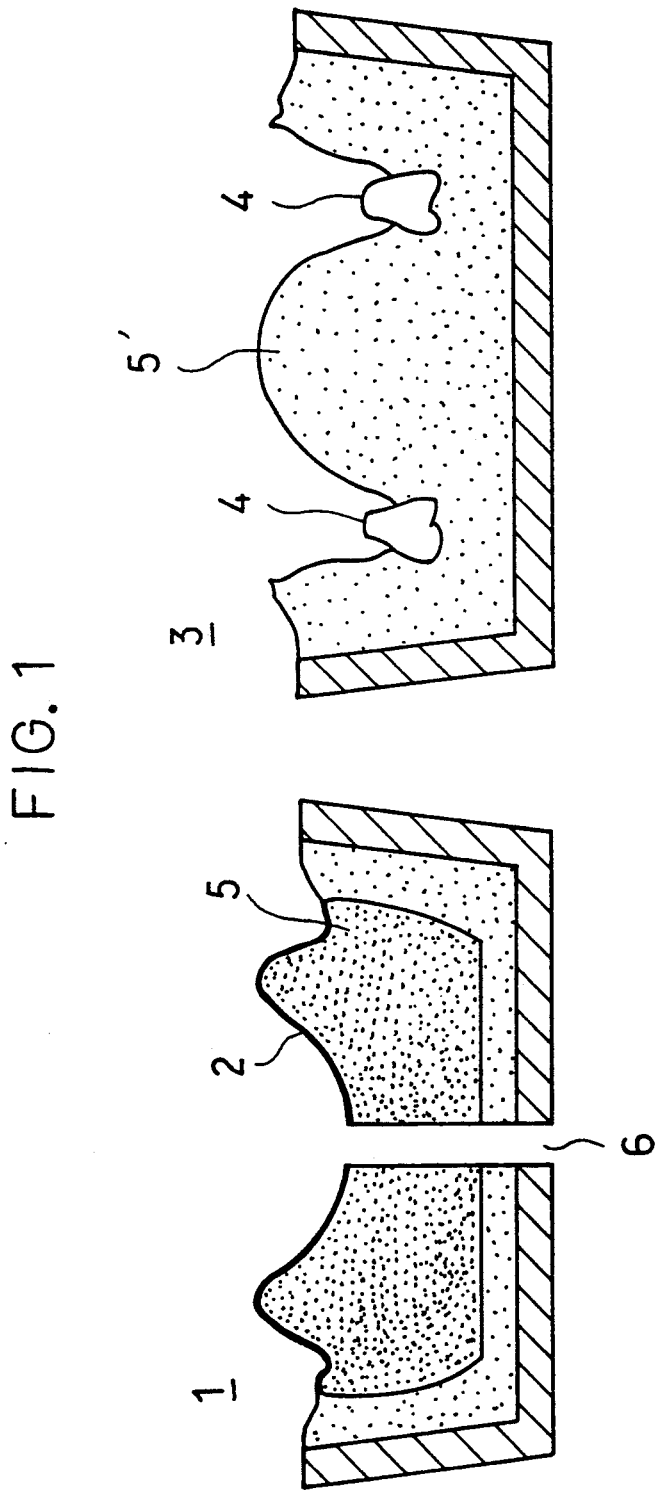
FIG. 1 is a vertically sectional view showing separated first half and second half shells.
Figure 2:
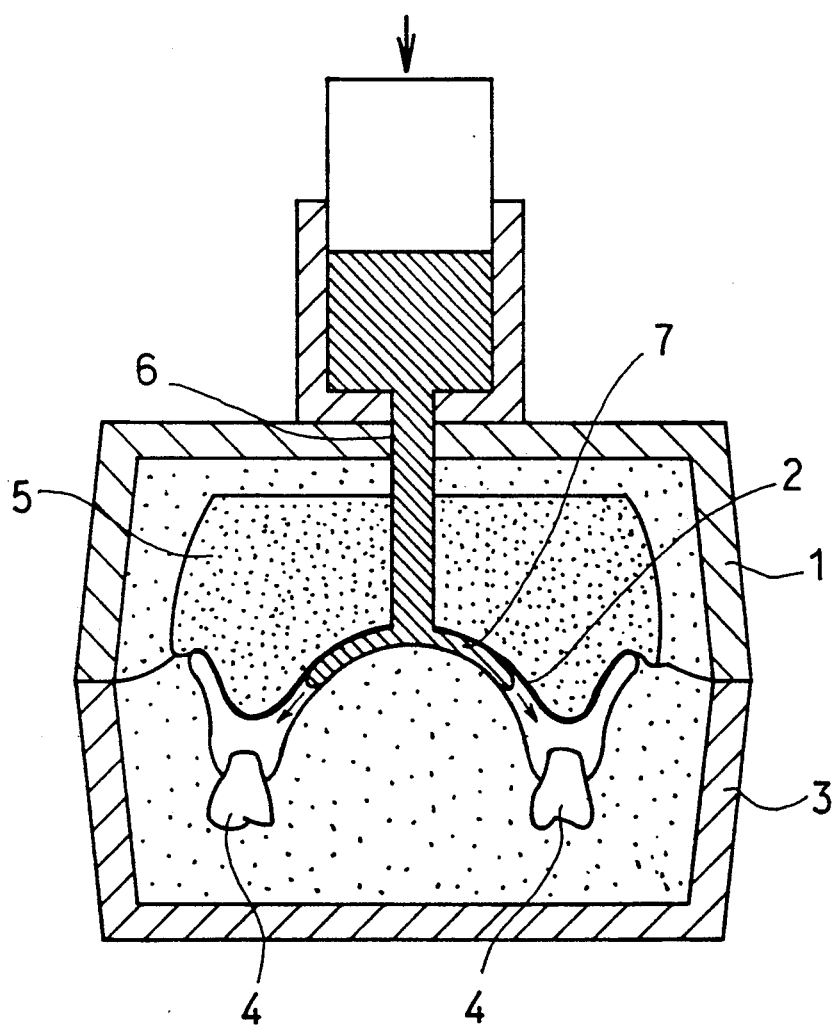
FIG. 2 is a vertically sectional view showing an assembly of half shells into which a dough-like resin is being supplied.
Figure 3:
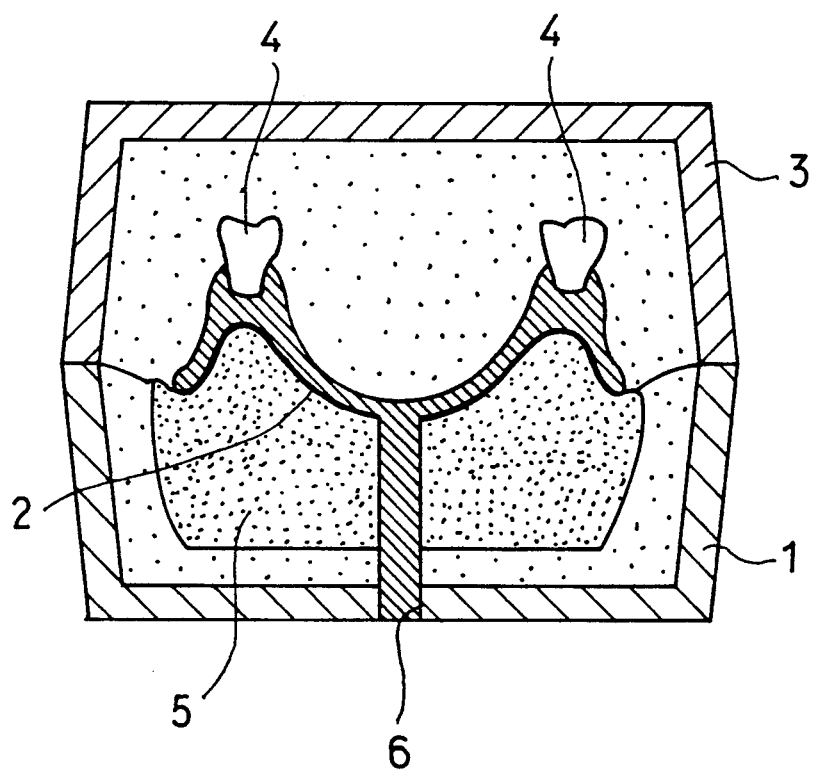
FIG. 3 is a vertically sectional view showing the assembly of half shells during the polymerization.

Referring to FIG. 1, a first half shell 1 includes a plaster cast 5 having a corresponding mucosal surface 2. The surface 2 is depicted with a thick line for clarity. Indicated at 3 is a second half shell. The illustrated half shells 1, 3 are in a stage after completion of flasking and wax elimination. The second half shell 3 has artificial teeth 4 embedded in a plaster cast 5'. The first half shell 1 is provided with a sprue 6 for forcing a dough-like resin into the flask therethrough. These half shells 1, 3 are of a conventional structure.

The half shells 3 are heated to a temperature required for the polymerization of a dough-like heat-curable resin by a suitable method, for example, by employing a constant temperature oven. Preferably the first half shell 1 is heated to a higher temperature level, e.g. 120° C., in the range of the temperature for polymerizing the dough-like resin and the second half shell 3 is heated to a lower temperature level, e.g. 70° C., in said range than the first half shell 1.

After the half shells 1, 3 have been superposed into an assembly, a dough-like resin 7 is forced into the assembly through the sprue 6 by a per se conventional method. After charging the resin 7, the assembly of half shells 1, 3 combined is disposed with the first shell 1 placed at a lower position and the second shell 3 at an upper position, and is left in this state for the polymerization of the resin 7.

In this way, a plate denture is produced which has a uniformly polymerized mucosal surface of dimensionally precise configuration. After completion of polymerization, the obtained plate denture is withdrawn from the assembly by a conventional method and then polished.

What is claimed is:

1. A method for producing a plate denture, comprising the steps of:

heating a flask to a temperature level in a range of temperature for polymerizing a heat-curable resin, the flask being an assembly including a first half shell having a plaster cast with a corresponding mucosal surface and a second half shell having a plaster cast with artificial teeth embedded therein;

placing the heat-curable resin into the heated flask for polymerization while the flask is at the temperature level for polymerizing the heat-curable resin caused by the heating of the flask; and polymerizing the heat-curable resin in the heated flask to form the plate denture;

wherein during the step of heating the flask the first half shell is heated to a higher temperature level in the range of temperature for polymerizing the heat-curable resin than the second half shell, which second half shell is heated to a lower temperature level in the range of temperature for polymerizing the heat-curable resin.

2. A method as defined in claim 1, further including orienting the assembly of first and second half shells combined, with the first half shell placed at a lower position below the second half shell and the second half shell placed at an upper position above the first half shell, and maintaining the assembly in this orientation during the polymerization of the resin.

3. A method as defined in claim 1, wherein the higher temperature level is 120° C. and the lower temperature level is 70° C.

* * * * *